(12) United States Patent
Yokoi (10) Patent No.: US 9,370,802 B2
(45) Date of Patent: Jun. 21, 2016

(54) CLEANING AND STERILIZING METHOD FOR ULTRAPURE WATER MANUFACTURING SYSTEM

(75) Inventor: Ikunori Yokoi, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 1220 days.

(21) Appl. No.: 12/450,502

(22) PCT Filed: Mar. 27, 2008

(86) PCT No.: PCT/JP2008/055859
§ 371 (c)(1),
(2), (4) Date: Oct. 20, 2009

(87) PCT Pub. No.: WO2008/123351
PCT Pub. Date: Oct. 16, 2008

(65) Prior Publication Data
US 2010/0032387 A1    Feb. 11, 2010

(30) Foreign Application Priority Data

Mar. 30, 2007  (JP) ................................ 2007-091667

(51) Int. Cl.
*B08B 9/00* (2006.01)
*B08B 3/08* (2006.01)
(Continued)

(52) U.S. Cl.
CPC . *B08B 3/08* (2013.01); *A61L 2/183* (2013.01); *A61L 2/186* (2013.01); *A61L 2202/17* (2013.01); *C02F 2103/04* (2013.01); *C02F 2303/04* (2013.01); *C02F 2303/16* (2013.01)

(58) Field of Classification Search
CPC ........... B08B 3/08; A61L 2/183; A61L 2/186; A61L 2202/17; C02F 2103/04; C02F 2303/04; C02F 2303/16
USPC ............ 134/22.1, 22.11, 22.13, 22.17, 22.19, 134/26, 27, 29, 30, 34, 35, 36, 42; 510/247, 510/252
See application file for complete search history.

(56) References Cited

U.S. PATENT DOCUMENTS 5,526,841  A  *  6/1996  Detsch et al. .............. 137/15.04
6,840,251  B2 *  1/2005  Gill et al. ................... 134/22.12
(Continued)

FOREIGN PATENT DOCUMENTS

JP    H07-299126    11/1995
JP    2000-317413    11/2000
(Continued)

*Primary Examiner* — Bibi Carrillo
*Assistant Examiner* — Sharidan Carrillo
(74) *Attorney, Agent, or Firm* — Manabu Kanesaka (57) ABSTRACT

In a method of cleaning and sterilizing an ultrapure water manufacturing system including an ultrapure water manufacturing apparatus, a point of use of ultrapure water, and an ultrapure water channel connecting the ultrapure water manufacturing apparatus and the point of use, a cleaning and sterilizing process including an alkali cleaning step for cleaning at least part of the inside of the system with alkaline solution and a sterilizing step for sterilizing the system with sterile water after the alkali cleaning is treated twice or more. By treating the cleaning and sterilizing process twice or more, metals, organic substances, particles, and bacteria inside the ultrapure water manufacturing system can be highly efficiently removed, and thereby ultrapure water satisfying required water quality can be produced within a short period of time after the cleaning and sterilizing.

16 Claims, 3 Drawing Sheets

(51) Int. Cl.
*A61L 2/18* (2006.01)
*C02F 103/04* (2006.01)

(56) References Cited

U.S. PATENT DOCUMENTS

| | | | |
|---|---|---|---|
| 7,922,933 B2 * | 4/2011 | Martin | 252/187.21 |
| 2002/0137650 A1 * | 9/2002 | Okumura | 510/247 |
| 2003/0139311 A1 * | 7/2003 | Biering et al. | 510/302 |
| 2003/0203827 A1 * | 10/2003 | Cooper et al. | 510/247 |
| 2007/0009376 A1 * | 1/2007 | Hamada et al. | 422/20 |

FOREIGN PATENT DOCUMENTS

| | | | |
|---|---|---|---|
| JP | 2002-166283 | | 6/2002 |
| JP | 2002-192162 | | 7/2002 |
| JP | 2004-267864 | | 9/2004 |
| JP | 2004267864 | * | 9/2004 |
| JP | 2004-275881 | | 10/2004 |

* cited by examiner

CLEANING AND STERILIZING METHOD FOR ULTRAPURE WATER MANUFACTURING SYSTEM

FIELD OF THE INVENTION

The present invention relates to a method of cleaning and sterilizing an ultrapure water manufacturing system, and particularly relates to a method for highly cleaning contamination due to metals, organic substances, particles, and bacteria in an ultrapure water manufacturing system in fields such as electronic industry by efficiently cleaning and sterilizing the system.

BACKGROUND OF THE INVENTION

In the electronic industry field, ultrapure water is used for cleaning water of materials and parts. In particular, the quality of ultrapure water used in a semiconductor manufacturing factory or a wafer manufacturing factory is strictly controlled, for example, resistivity: 18.2 MΩ·cm or more, number of particles having a diameter of 50 nm or more: one/mL or less, number of bacterium: one/L or less, TOC (total organic carbon): 1 μg/L or less, ionic silica: 0.1 μg/L or less, metals: 1 ng/L or less, and ions: 5 ng/L or less.

The place where ultrapure water is used (point of use) is connected to an ultrapure water manufacturing apparatus and ultrapure water supply piping (channel), and residual ultrapure water that is not used at the point of use returns to the ultrapure water manufacturing apparatus through another ultrapure water supply piping, resulting in formation of a circulatory system to configure an ultrapure water manufacturing system as a whole.

Conventionally, cleaning with alkaline solution is used when an ultrapure water manufacturing system is newly or additionally set, modified, or maintained so that particles such as dust, silica, and aluminum in the air that exists into the system, particles included in water, such as remains of bacteria and rust, refuses which occurred during the system production, such as a filter, piping and more (hereinafter, these are collectively referred to as "particles") are properly eliminated to the outside of the system, and the number of particles having a diameter of 50 nm or more in one milliliter of ultrapure water is one or less (for example, Patent Document 1).

In addition, a method of sterilizing an ultrapure water manufacturing system in order to suppress bacteria in ultrapure water is proposed (Patent Documents 2 and 3).

Furthermore, a method of cleaning and sterilizing an ultrapure water manufacturing system by cleaning the inside of the ultrapure water manufacturing system with alkaline solution and then with hydrogen peroxide solution is proposed (Patent Document 4).

Incidentally, the principle of removing particles with the alkaline solution is as follows.

The adhesion of particles to piping and others of an ultrapure water manufacturing system is electrical, i.e., electrostatical due to the surface potential. In general, the surface potential of particles in solution such as cleaning fluid varies depending on the solution characteristics and, particularly, can be significantly changed by varying the pH of the solution. A shift in the pH of the solution to the alkaline side makes the particles negatively charged and also makes the charge increase. However, no change in surface potential of an organic polymer material, such as PVC (polyvinyl chloride) or PPS (polyphenylene sulfide), forming the piping system and the like of the ultrapure water manufacturing system is caused, and the material has negative charge regardless of the pH change of the fluid in contact therewith. Therefore, the particles negatively charged by shifting the pH of the fluid in contact therewith are electrically repelled from the material forming the system and are easily peeled and removed.

Furthermore, the peeling and removing action can be sufficiently achieved even if the concentration of alkaline solution used as the cleaning fluid is low (for example, several tens milligrams per liter). Therefore, the cleaning fluid can be used at a low concentration. Consequently, the ratio that a component of the cleaning fluid remains in the system is reduced, and the increase of TOC by cleaning fluid is inhibited. As a result, the cleaning work can be finished within a short period of time, and the build-up of the quality of ultrapure water produced by the ultrapure water manufacturing system is possible.

Since the method for cleaning an ultrapure water manufacturing system with alkaline solution is excellent for removal efficiency of particles, particles adhering in the ultrapure water manufacturing system can be promptly peeled and removed. In addition, since the concentration of the cleaning fluid is low, the component of the cleaning fluid hardly remains after cleaning, and thereby TOC is hardly increased. Therefore, the cleaning work can be performed within a short period of time.

In Patent Document 4, efficient cleaning and sterilizing is possible by the cleaning and sterilizing method in which hydrogen peroxide is further injected for sterilization after the cleaning with alkaline solution.

Patent Document 1: Japanese Unexamined Patent Application Publication No. 2000-317413

Patent Document 2: Japanese Unexamined Patent Application Publication No. 2002-166283

Patent Document 3: Japanese Unexamined Patent Application Publication No. 2004-275881

Patent Document 4: Japanese Unexamined Patent Application Publication No. 2002-192162

SUMMARY OF THE INVENTION

When the method of cleaning and sterilizing an ultrapure water manufacturing system of Patent Document 4 is applied to a new or additional ultrapure water manufacturing system, and production of ultrapure water is started after the cleaning and sterilizing treatment, immediately after the cleaning and sterilizing, a required ultrapure water quality that the number of bacteria in one liter of the ultrapure water is one or less can be satisfied, but it takes 2 weeks for satisfying a required ultrapure water quality that the number of particles having a diameter of 50 nm or more in one milliliter of the ultrapure water is one or less, and also it takes 2 weeks for satisfying a required ultrapure water quality that the concentration of metals is 1 ng/L or less.

However, recently, a new or additional ultrapure water system has been being demanded to satisfy required ultrapure water qualities within one week after cleaning and sterilizing treatment. Therefore, it is a situation that the method of cleaning and sterilizing an ultrapure water manufacturing system proposed in Patent Document 4 cannot comply with such requirements.

Accordingly, it is an object of the present invention to provide a method of cleaning and sterilizing an ultrapure water manufacturing system, wherein metals, organic substances, particles, and bacteria inside the ultrapure water manufacturing system can be highly efficiently removed, and thereby ultrapure water satisfying required water qualities can be produced within a short period of time after cleaning and sterilizing.

The present inventors have conducted intensive investigations for solving the above-mentioned problems and, as a result, have found the fact that by treating a cleaning and sterilizing process including cleaning with alkaline solution and then sterilizing with sterile water twice or more, contaminants such as metals and microorganisms can be highly removed and the period from the start of ultrapure water production after the cleaning and sterilizing till the required water qualities are satisfied (hereinafter, sometimes referred to as "build-up period") can be shortened to within one week even in the requirement items that take 2 weeks as the build-up periods in the conventional methods.

The present invention has been achieved based on these findings, wherein in a method of cleaning and sterilizing an ultrapure water manufacturing system including an ultrapure water manufacturing apparatus, a point of use of ultrapure water, and an ultrapure water channel connecting the ultrapure water manufacturing apparatus and the point of use, a cleaning and sterilizing process including an alkali cleaning step for cleaning at least part of the inside of the system with alkaline solution and a sterilizing step for sterilizing the system with sterile water after the alkali cleaning is treated twice or more.

According to the method of cleaning and sterilizing an ultrapure water manufacturing system of the present invention, the build-up period can be significantly shortened by highly removing metals, organic substances, particles, and bacteria inside the ultrapure water manufacturing system.

DETAILED DESCRIPTION OF THE INVENTION

Embodiments of the method of cleaning and sterilizing an ultrapure water manufacturing system of the present invention will be described below.

In a method of cleaning and sterilizing an ultrapure water manufacturing system including an ultrapure water manufacturing apparatus, a point of use of ultrapure water, and an ultrapure water channel connecting the ultrapure water manufacturing apparatus and the point of use, a cleaning and sterilizing process including an alkali cleaning step for cleaning at least part of the inside of the system with alkaline solution and a sterilizing step for sterilizing the system with sterile water after the alkali cleaning is treated twice or more.

In the method of cleaning and sterilizing an ultrapure water manufacturing system of the present invention, the cleaning and sterilizing process including the alkali cleaning step and the sterilizing step is treated twice or more, and the method preferably includes a first flushing step for cleaning the inside of the system with flushing water consisting of primary pure water or ultrapure water between the alkali cleaning step and the sterilizing step. In addition, the method preferably includes a second flushing step for cleaning the inside of the system with flushing water consisting of primary pure water or ultrapure water immediately after the sterilizing step. That is, one cycle of the cleaning and sterilizing process according to the present invention preferably includes at least four steps: the alkali cleaning step, the first flushing step, the sterilizing step, and the second flushing step, in this order.

In the present invention, the alkaline solution used in the alkali cleaning step is preferably a water solution prepared by dissolving one or more of alkaline compounds selected from the group consisting of ammonia, ammonium compounds, hydroxides of alkali metals, and oxides of alkali metals, in particular, a water solution prepared by dissolving an ammonium salt and/or a hydroxide of an alkali metal. The alkaline solution is most preferably a water solution prepared by dissolving ammonia, an ammonium salt, a tetraalkylammonium compound, sodium hydroxide, potassium hydroxide, or the like. In addition, the solvent is preferably deionized water, more preferably primary pure water or ultrapure water.

The peeling efficiency of particles is low when the pH of the alkaline solution used in the alkali cleaning step is less than a certain value, i.e., when the pH is less than 9. However, a too high pH of the alkaline solution may corrode piping and other components of the system and also has a problem that the subsequent first flushing has to be treated for a long period of time. Therefore, the pH of the alkaline solution used in the alkali cleaning has preferred upper and lower limits.

Specifically, the alkaline solution preferably has a pH of 9 to 12, more preferably a pH of 9.5 to 11.

The temperature of the alkaline solution is not particularly limited, but is preferably 20° C. or more and 40° C. or less with consideration of the resistance of parts constituting the ultrapure water manufacturing system.

When the sterile water used in the sterilizing step is primary pure water or ultrapure water, the sterile water is preferably hot pure water having a temperature of 60° C. or more. A higher temperature within a range of not exceeding the heat resistance temperatures of the parts and piping constituting the ultrapure water manufacturing system is preferred at the point of the cleaning effect, as in the alkaline solution. In the case of PVDF having a heat resistance temperature of about 80° C., the temperature of the sterile water may be 75 to 80° C., and in the case using stainless steel as the constitutional material, cleaning can be treated at a temperature of about 100° C.

When the sterilization cannot be treated at a high temperature because of low heat resistance of the material of the piping or another component, it is preferred to use ozone water or hydrogen peroxide water to prevent contamination with impurities in the subsequent stage. The control of ozone water concentration is difficult, and, in some cases, the piping and the like may be corroded by its too strong oxidizability. Accordingly, it is more preferred to use hydrogen peroxide water. The sterilizing power of hydrogen peroxide water is determined by balance between hydrogen peroxide concentration and solution temperature. Therefore, a necessary sterilizing power can be obtained by increasing the hydrogen peroxide concentration even if the solution temperature is low. However, since a higher concentration of hydrogen peroxide makes the period of time necessary for the subsequent second flushing step longer, an excessively high concentration is undesirable.

Therefore, the hydrogen peroxide concentration of the hydrogen peroxide water used has a predetermined preferred range. Specifically, the concentration is preferably 0.01 to 10% by weight, in particular, 0.01 to 5.0% by weight. In addition, the solvent of the hydrogen peroxide water is preferably deionized water, more preferably primary pure water or ultrapure water.

Furthermore, the temperature of hydrogen peroxide water as the sterile water is preferably in a range of 10 to 50° C. and is properly determined according to the hydrogen peroxide concentration and the heat resistance temperatures of the parts and piping constituting the ultrapure water manufacturing system. The temperature lower than 10° C. cannot provide sufficient sterilizing effect, and also a device for producing cold water with the temperature below 10° C. is additionally necessary, which is high cost. Thus, there is no advantage. The temperature higher than 50° C. causes decomposition of hydrogen peroxide, resulting in a significant decrease in sterilizing effect. As described above, even if the temperature of sterile water is low, sufficient sterilizing effect can be obtained by using hydrogen peroxide water. Therefore, when the constitutional material of the ultrapure water manufacturing system is low in heat resistance, it is preferred to use hydrogen peroxide water as the sterile water.

In a combination of the hydrogen peroxide concentration and the temperature of hydrogen peroxide water for providing sufficient sterilizing effect, a preferred fluid temperature corresponding to a hydrogen peroxide concentration of 0.01 to 0.5% by weight is 30 to 50° C., and a preferred fluid temperature corresponding to a hydrogen peroxide concentration of 0.5 to 5.0% by weight is 10 to 30° C.

In the alkali cleaning step and the immediately following first flushing step, too slow flow rates of the alkaline solution and the flushing water cause a problem that particles peeled by the alkali cleaning adhere again to the piping or another component. Therefore, the flow rates of the alkaline solution used in the alkali cleaning and the flushing water used in the first flushing are preferably held at predetermined levels or more. The flow rates held at predetermined levels or more also have an advantage that a turbulent flow is generated and thereby particles staying at a fluid remaining portion in the system can be promptly removed.

However, an excessively high flow rate has a problem of an increase in loss of pressure and may cause breakage (leakage) due to vibration of the junction area of the piping or another component. Therefore, the flow rate has a preferred upper limit.

Specifically, the flow rates of the alkaline solution used in the alkali cleaning step and the flushing water used in the first flushing step are each preferably held at 0.3 to 2.0 m/sec, more preferably 0.5 to 1.5 m/sec.

Furthermore, the flow rate of the flushing water used in the second flushing step immediately after the sterilizing step is preferably held at a predetermined level or more in order to reliably discharge remains of bacteria from the system. However, as in the above, an excessively high flow rate has a problem of an increase in loss of pressure and may cause breakage (leakage) due to vibration of the junction area of the piping or another component. Therefore, the flow rate has a preferred upper limit. Specifically, the flow rate of the flushing water used in the second flushing step is preferably held at 0.3 to 2.0 m/sec, more preferably 0.5 to 1.5 m/sec.

On the other hand, since it is desirable to infiltrate the sterile water into the system, the flow rate of the sterile water used in the sterilizing step may be slower than those of the alkaline solution and the flushing water. However, since an excessively high flow rate has a problem of an increase in loss of pressure and may cause breakage (leakage) due to vibration of the junction area of the piping or another component, the flow rate has a preferred upper limit, as in the alkaline solution and the flushing water. Specifically, the flow rate of the sterile water is preferably held at 0.1 to 2.0 m/sec, more preferably 0.3 to 1.5 m/sec.

In the case that the first flushing step is performed after the alkali cleaning, the completion of the flushing can be determined by the pH of the flushing water, specifically, when the pH of flushing water in ultrapure water supply piping (channel 3b in the below-mentioned FIG. 3) for returning the flushing water that has been sent to the point of use to the ultrapure water manufacturing apparatus reaches a predetermined level of 8 or less, for example, a pH of 6.0 to 8.0. Alternatively, the completion of the flushing can be determined by the resistivity of the flushing water, specifically, when the resistivity of flushing water in ultrapure water supply piping (channel 3b in the below-mentioned FIG. 3) for returning the flushing water that has been sent to the point of use to the ultrapure water manufacturing apparatus reaches a predetermined level of 10 MΩ·cm or more, for example, 10.0 to 18.2 MΩ·cm.

Furthermore, in the case that the second flushing step is performed after sterilization with hydrogen peroxide water, the completion of the flushing can be confirmed by the hydrogen peroxide concentration in the flushing water, specifically, when the hydrogen peroxide concentration in flushing water in ultrapure water supply piping (channel 3b in the below-mentioned FIG. 3) for returning the flushing water that has been sent to the point of use to the ultrapure water manufacturing apparatus is reduced to 1 mg/L or less, that is, no hydrogen peroxide is detected. Here, the conclusion that no hydrogen peroxide is detected refers to, for example, that no change in color of hydrogen peroxide test paper is observed when the test paper is saturated with the flushing water or that a measurement value of a hydrogen peroxide concentration meter by an iodine coulometric titration method is reduced to 1 mg/L or less.

Furthermore, in the case that the second flushing step is performed after sterilization with hot pure water, the completion of the flushing can be determined when the resistivity of flushing water in ultrapure water supply piping (channel 3b in the below-mentioned FIG. 3) for returning the flushing water that has been sent to the point of use to the ultrapure water manufacturing apparatus reaches a predetermined level of 10.0 MΩ·cm or more, for example, 10.0 to 18.2 MΩ·cm.

The flushing may be terminated according to the time schedule without treating the above-mentioned determination of completion, but in such a case, since it is necessary to consider the remaining of chemicals such as the alkaline solution and the sterile water or impurities generated by the cleaning and sterilizing, the period of time till the termination of flushing must include a certain level of buffer. Therefore, the period of time till the termination of flushing becomes longer than those in the cases that the completion is determined as in above, and the amount of flushing water used is increased with it, which is very inefficient.

In the present invention, the cleaning and sterilizing process including the alkali cleaning step and the sterilizing step and preferably including the alkali cleaning step, the first flushing step, the sterilizing step, and the second flushing step is treated twice or more. The period of time for a first cycle of the cleaning and sterilizing process (the period of time necessary for the cleaning and sterilizing process means the total time for the alkali cleaning step and the sterilizing step, not including the time for the first and second flushing steps) is preferably shorter than the period of time for a second or later cycle of the cleaning and sterilizing process. More preferably, the period of time for the alkali cleaning step and the period of time for the sterilizing step in the first cycle of the cleaning and sterilizing process are set to be respectively shorter than those in the second or later cycle of the cleaning and sterilizing process.

This is based on the following reasons.

That is, in the alkali cleaning step in the first cycle of the cleaning and sterilizing process, a large amount of impurities, such as particles adhering to the piping and other components in the system, reacts with a large amount of alkali and is thereby peeled. Therefore, the concentration of the alkali is decreased, which reduces the cleaning performance and also may make the impurities such as particles adhere again to the piping or another component in the system. In addition, if the alkali cleaning step in the first cycle of the cleaning and sterilizing process is long, the large amount of the particles that have been peeled chemically reacts with the piping or another component in the system under the alkali condition, which may degrade the parts constituting the ultrapure water manufacturing system. Accordingly, it is preferred that the alkali cleaning step in the first cycle of the cleaning and sterilizing process be performed for roughly removing impurities such as particles by setting the cleaning time short and discharging the cleaning drain early and that the alkali cleaning step in the second or later cycle of the cleaning and sterilizing process be performed for highly cleaning by spending enough time.

On the other hand, in the sterilizing step of the first cycle of the cleaning and sterilizing process, a metal adhering on the surface or infiltrating in the surface layer of nonmetallic parts constituting the ultrapure water manufacturing system is eluted as metal ions by the oxidizing power of the sterile water (hot pure water also has oxidizing power due to high temperature thereof). The metal ions physically erode or elute and thereby readily degrade parts made of a material that is different from that of the parts from which the metal ions themselves are eluted. Accordingly, it is preferred that the sterilizing step in the first cycle of the cleaning and sterilizing process be performed for roughly removing metal ions eluted from nonmetallic parts by setting the sterilizing time short and discharging the sterilization drain early and that the sterilizing step in the second or later cycle of the cleaning and sterilizing process is performed for a period of time sufficient for a high level of sterilization. Incidentally, examples of nonmetal of the nonmetallic parts herein include silicon, PVC (polyvinyl chloride), PPS (polyphenylene sulfide), PVDF (polyvinyl difluoride), FRP (fiber-reinforced plastic), PFA (tetrafluoroethylene/perfluoroalkyl vinyl ether copolymer), EPOM (ethylene propylene diene terpolymer), and Viton (registered trademark) (fluoro rubber, manufactured by DuPont Elastomer Co., Ltd.).

In this case, for example, it is preferred that the period of time for the alkali cleaning step (circulation time of the below-described alkaline solution in the system) in the first cycle of the cleaning and sterilizing process be set to 0.5 to 2.0 hours, for example, 1 hour; the period of time for the subsequent sterilizing step (circulation time of the below-described sterile water in the system) be set to 0.5 to 2.0 hours, for example, 1 hour; the period of time for the alkali cleaning step in the second or later cycle of the cleaning and sterilizing process be set to 1 to 3 hours, for example, 2 hours, so as to be about 1.5 to 2 times that for the alkali cleaning step in the first cycle of the cleaning and sterilizing process; and the period of time for the subsequent sterilizing step be set to 1 to 3 hours, for example, 2 hours, so as to be about 1.5 to 2 times that for the sterilizing step in the first cycle of the cleaning and sterilizing process.

Furthermore, the primary pure water or ultrapure water in the present invention is defined as follows:

primary pure water: a resistivity of 10 MΩ·cm or more, 100 μg/L or less of TOC; and ultrapure water: a resistivity of 15 MΩ·cm or more, 1 μg/L or less of TOC, 1 ng/L or less of metals.

By thus controlling the length of the cleaning time, the build-up period after the cleaning and sterilizing treatment can be further certainly shortened.

The present invention will now be more specifically described with reference to the drawings.

Figure 1:
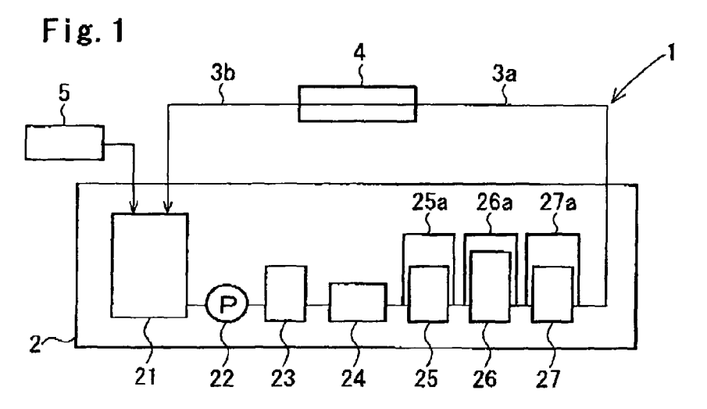
FIG. 1 is a flow diagram of an ultrapure water manufacturing system showing an embodiment of the method of cleaning and sterilizing an ultrapure water manufacturing system of the present invention.

FIG. 1 is an example of a flow diagram showing an embodiment of the method of cleaning and sterilizing an ultrapure water manufacturing system of the present invention.

The ultrapure water manufacturing system 1 is composed of an ultrapure water manufacturing apparatus 2, a point of use 4 of ultrapure water, and ultrapure water channels (piping or tubes) 3a and 3b connecting them. The ultrapure water produced by the ultrapure water manufacturing apparatus 2 is sent to the point of use 4 through the channel 3a and is partially used at the point of use 4, and the remaining ultrapure water not used returns to the ultrapure water manufacturing apparatus 2 through the channel 3b to form a circulatory system.

The ultrapure water manufacturing apparatus (secondary pure water apparatus) 2 is composed of a combination of a tank 21, a pump 22, a heat exchanger 23, a low-pressure ultraviolet oxidation device 24, a deaerator 25, an ion exchanger 26, and an ultrafiltration membrane (UF) device 27. These devices are connected with piping or tubes. In some cases, the ultrapure water manufacturing apparatus may further include a membrane separation device including reverse osmosis (RO) membrane, an oxidant-removing device, and an ion exchanger that is different from or similar to the ion exchanger 26.

In the embodiment shown in FIG. 1, the tank 21 is disposed on the entrance side of the ultrapure water manufacturing apparatus 2 and receives primary pure water from a primary pure water manufacturing apparatus 5 and ultrapure water returning through the ultrapure water supply piping 3b. The pump 22 supplies raw water for ultrapure water received in the tank 21 for treatment with the heat exchanger 23, the low-pressure ultraviolet oxidation device 24, the deaerator 25, the ion exchanger 26, and the ultrafiltration membrane device 27, in series, for producing ultrapure water.

In addition, the primary pure water can be obtained, for example, by treating raw water with a reverse osmosis membrane device, then with an ion exchanger, and further with reverse osmosis membrane.

The point of use 4 indicates the place where ultrapure water is used. The point of use 4 does not have any particular limitation on the conditions.

Specifications of the piping or tubes used in the ultrapure water manufacturing apparatus 2 and the piping/tubes of the channels 3a and 3b are not particularly limited, as long as the component thereof is hot eluted into ultrapure water. For example, PVC (polyvinyl chloride), PPS (polyphenylene sulfide), PVDF (polyvinyl difluoride), FRP (fiber-reinforced plastic), PFA (tetrafluoroethylene/perfluoroalkyl vinyl ether copolymer), EPDM (ethylene propylene diene terpolymer), or Viton (registered trademark) (fluoro rubber, manufactured by DuPont Elastomer Co., Ltd.) can be used.

In order to clean such an ultrapure water manufacturing system 1, the deaerator 25, the ion exchanger 26, and the ultrafiltration membrane device 27 of the ultrapure water manufacturing apparatus 2 may be provided with bypass piping 25a, 26a, and 27a, respectively. In some cases, the heat exchanger 23 and the low-pressure ultraviolet oxidation device 24 also may be provided with bypass piping.

In the cleaning and sterilizing of the ultrapure water manufacturing system 1, first, valves are set to bypass the deaerator 25, the ion exchanger 26, and the ultrafiltration membrane device 27, and the water level of the tank 21 is adjusted. When the heat exchanger 23 and the ultraviolet oxidation device 24 are also provided with bypass piping, the lines thereof are slightly opened. Then, undiluted alkaline solution is poured into the tank 21 to change the ultrapure water in the ultrapure water manufacturing system to alkaline solution having a pH of 9 or more, and the pump 22 is operated for circulating the alkaline solution in the ultrapure water manufacturing system 1.

After the cleaning of the ultrapure water manufacturing system with the alkaline solution and before sterilization of the ultrapure water manufacturing system with sterile water, flushing is made by expelling the alkaline solution in the ultrapure water manufacturing system to the outside of the system using primary pure water supplied from the primary pure water manufacturing apparatus 5 as the flushing water. It is preferred that the flushing for expelling the alkaline solution be determined to be completed when the pH of the flushing water is reduced to 8 or less and/or the resistivity of the flushing water is increased to 10 MΩ·cm or more, and then the step be changed to the step of sterilizing the inside of the ultrapure water manufacturing system 1 with sterile water.

In the sterilization with sterile water, as in the cleaning with the alkaline solution, valves are set to bypass the deaerator 25, the ion exchanger 26, and the ultrafiltration membrane device 27, and the water level of the tank 21 is adjusted. When the heat exchanger 23 and the ultraviolet oxidation device 24 are provided with bypass piping, the lines are slightly opened. Then, ultrapure water in the ultrapure water manufacturing system is altered to sterile water by heating the ultrapure water with the heat exchanger 23 to necessary temperature or pouring hydrogen peroxide into the tank 21, according to need, and the pump 22 is operated to circulate the sterile water in the ultrapure water manufacturing system 1.

After sterilizing of the inside of the ultrapure water manufacturing system with the sterile water and before the subsequent cleaning of the ultrapure water manufacturing system with alkaline solution, flushing is made by expelling the sterile water in the ultrapure water manufacturing system to the outside of the system using primary pure water supplied from the primary pure water manufacturing apparatus 5 as the flushing water. Then, in the case that hydrogen peroxide is used as the sterile water, the flushing for expelling the hydrogen peroxide water is determined to be completed when the hydrogen peroxide concentration of the flushing water is reduced to 1 mg/L or less, and then the step can be changed to the second alkali cleaning step using alkaline solution.

Furthermore, in the case that hot pure water is used as the sterile water, the flushing is determined to be completed when the resistivity of the flushing water reaches a predetermined level of 10.0 MΩ·cm or more, for example, 10.0 to 18.2 MΩ·cm, and the step can be changed to the second alkali cleaning step using alkaline solution.

The second cleaning step using alkaline solution can be treated by the same operation and the same conditions as those in the first cleaning step using alkaline solution except that only the ion exchanger 26 is bypassed.

However, the second cleaning with alkaline solution is not necessarily performed under the same conditions as those of the first cleaning with alkaline solution. The pH and the temperature of the cleaning solution, the type of the alkaline compound used, and the flow rate and the time of circulation may be different.

After the second cleaning with alkaline solution, flushing is treated as in that after the first cleaning with alkaline solution, and then the step is changed to the second sterilizing step using sterile water.

The second sterilizing step using sterile water can be treated by the same operation and the same conditions as those in the first sterilizing step using sterile water except that only the ion exchanger 26 is bypassed.

However, the second sterilization with sterile water is not necessarily performed under the same conditions as those of the first sterilization with sterile water. The temperature and the type (hot water or hydrogen peroxide water, and in the case of hydrogen peroxide water, its concentration) of the sterile water and the flow rate and the time of circulation may be different.

After the second sterilization with sterile water, the flushing is treated as in that after the first sterilization with sterile water. Then, the step is changed to a third sterilizing step using alkaline solution, or the production of ultrapure water is restarted.

In the present invention, the cycle of the cleaning and sterilizing process, that is, a series of steps including the cleaning step using alkaline solution, the first flushing step, the sterilizing step using sterile water, and the second flushing step, may be treated three times or more, as long as the cleaning and sterilizing process is treated twice or more.

Thus, according to the method of cleaning and sterilizing an ultrapure water manufacturing system of the present invention in which the cleaning and sterilizing process including the cleaning with alkaline solution and the sterilization with sterile water is treated twice or more, in the production of ultrapure water after the cleaning and the sterilization, ordinarily, ultrapure water can be obtained after a build-up period of within about one week, though the build-up period in the method described in Patent Document 4 is 2 weeks.

EXAMPLES

The present invention will now be more specifically described with reference to an Example, Comparative Examples, and experimental examples.

Example 1

The ultrapure water manufacturing system shown in FIG. 1 was cleaned as follows.

First, ammonia water having a concentration of 50 mg/L was poured into the tank 21 of the ultrapure water manufacturing apparatus 2 to give a pH of 10.5. The resulting ammonia water was sent to the heat exchanger 23 at a flow rate of 1 m/sec using the pump 22 and was adjusted the temperature thereof to ordinary temperature. Then, the ammonia water was circulated in the ultrapure water manufacturing apparatus 2, the channel 3a, the point of use 4, and the channel 3b in order for one hour for cleaning the system. However, the cleaning fluid was bypassed through the bypass piping 25a, 26a, and 27a not to wash the deaerator 25, the ion exchanger 26, and the ultrafiltration membrane device 27.

Then, the cleaning fluid was discharged from blow-out piping (not shown). Primary pure water was supplied to the tank 21 as flushing water, and flushing was performed by circulating the primary pure water in the system at a flow rate of 1 m/sec for expelling the cleaning fluid remaining in the inside of the system.

This flushing was treated for one hour, and then when the pH of the flushing water in the channel 3b was reduced to 8, hydrogen peroxide was poured into the tank 21 so as to give a concentration of 0.1% by weight. The resulting hydrogen peroxide water was circulated at 1 m/sec for one hour. At this point, the temperature of the hydrogen peroxide water was set to 40° C.

Then, the flushing was treated for 2 hours as in above, and when the hydrogen peroxide water concentration was reduced to a level that hydrogen peroxide test paper could not detect, the first cycle of the cleaning and sterilizing process was terminated.

Then, the second cycle of the cleaning and sterilizing process was carried out, at the same concentrations and the same temperatures, by treating cleaning with ammonia water for 2 hours, flushing for one hour, sterilization with hydrogen peroxide water for 2 hours, and flushing for 2 hours.

After the termination of the cleaning, the ordinary operation was carried out, and the change in ultrapure water quality with the passage of time at the point of use 4 was investigated by measuring the number of particles. The number of particles in ultrapure water was measured with an analyzer according to a laser scattering system, and the number of particles in ultrapure water was counted by an on-line monitor that can monitor the number of particles having a diameter of 0.05 μm or more.

Figure 2:
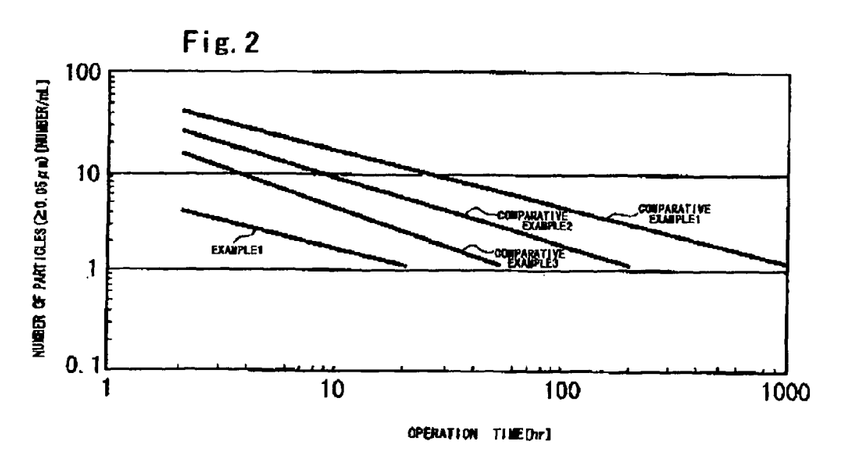
FIG. 2 is a graph showing changes in the number of particles in ultrapure water with the passage of time in Example 1 and Comparative Examples 1 to 3.

The results are shown in FIG. 2.

In addition, the ultrapure water at the point of use 4 was sampled 36 hours after the start of the ordinary operation, and the amount of metal impurities in the ultrapure water was measured by ICP-MS. The results are shown in Table 1.

Comparative Example 1

Cleaning was performed as in Example 1 except that only the sterilizing with hydrogen peroxide water and the subsequent flushing were made, without the cleaning with ammonia water, in the first cycle of the cleaning and sterilizing process, and the second cycle of the cleaning and sterilizing process was not made (that is, only the sterilization was made once). Then, similarly, the change in the number of particles with the passage of time in the ultrapure water at the point of use was investigated. The results are shown in FIG. 2.

Comparative Example 2

Cleaning and sterilization were performed as in Example 1 except that only the first cycle of the cleaning and sterilizing process was made and the second cycle of the cleaning and sterilizing process was not made. Then, similarly, the change in the number of particles with the passage of time in the ultrapure water at the point of use was investigated. The results are shown in FIG. 2.

Cleaning and sterilization were performed as in Example 1 except that only the first cycle of the cleaning and sterilizing process was treated and the second cycle of the cleaning and sterilizing process was not treated. Then, similarly, the change in the number of particles with the passage of time in the ultrapure water at the point of use was investigated. The results are shown in FIG. 2.

In addition, similarly, the amount of metal impurities in the ultrapure water 36 hours after the start of operation was investigated. The results are shown in Table 1.

Comparative Example 3

Cleaning and sterilization were performed as in Example 1 except that only the cleaning with ammonia water and the subsequent flushing were made, without the sterilization with hydrogen peroxide water, in the first cycle of the cleaning and sterilizing process. Then, similarly, the change in the number of particles with the passage of time in the ultrapure water at the point of use was investigated. The results are shown in FIG. 2.

As obvious from FIG. 2, in Comparative Example 1 in which only sterilization with hydrogen peroxide water was made, it took 1000 hours to reduce the number of particles having a diameter of 0.05 μm or more in the ultrapure water to one per milliliter or less.

Furthermore, in Comparative Example 2 in which the cleaning and sterilizing process including the cleaning with ammonia water and the sterilization with hydrogen peroxide water was made only once, it took 200 hours or more to reduce the number of particles having a diameter of 0.05 μm or more in the ultrapure water to one per milliliter or less.

In Comparative Example 3 in which cleaning with ammonia water was made and then the cleaning and sterilizing process including the cleaning with ammonia water and the sterilization with hydrogen peroxide water was further made, it took 60 hours to reduce the number of particles having a diameter of 0.05 μm or more in the ultrapure water to one per milliliter or less.

On the other hand, in Example 1 in which the cleaning and sterilizing process including the cleaning with ammonia water and the sterilization with hydrogen peroxide water was made twice, the period of time necessary for reducing the number of particles having a diameter of 0.05 μm or more in the ultrapure water to one per milliliter or less was 20 hours, which reveals that the build-up period could be significantly shortened.

Incidentally, the build-up period herein is defined as the period of time necessary for satisfying the requirement that the number of particles having a diameter of 0.05 μm or more in ultrapure water is one per milliliter or less when the production of ultrapure water is started after the termination of various cleaning and sterilization of a newly set sub-system (secondary pure water manufacturing apparatus).

Comparative Example 4

Cleaning and sterilization were performed as in Example 1 except that only the sterilization and the subsequent flushing were made, without the alkali cleaning, in the second cycle of the cleaning and sterilizing process. Then, similarly, the build-up period was investigated from the change in the number of particles with the passage of time in the ultrapure water at the point of use and was found to be 180 hours.

Comparative Example 5

Cleaning and sterilization were performed as in Example 1 except that only the sterilization and the subsequent flushing were made, without the alkali cleaning, in the first cycle of the cleaning and sterilizing process. Then, similarly, the build-up period was investigated from the change in the number of particles with the passage of time in the ultrapure water at the point of use and was found to be 180 hours.

Table 2 shows the results of the above described Example 1 and Comparative Examples 1 to 5.

TABLE 1

|  |  | Example 1 | Comparative Example 2 |
|---|---|---|---|
| Metal concentration in ultrapure water (ng/L) | Na | 0.4 | 1.2 |
|  | Al | <0.1 | 0.2 |
|  | K | 0.1 | 0.2 |

TABLE 1-continued

|   | Example 1 | Comparative Example 2 |
|---|---|---|
| Ca | 0.4 | 0.6 |
| Fe | 0.2 | 0.4 |
| Ni | <0.1 | 0.2 |
| Cu | <0.1 | 0.1 |
| Zn | <0.1 | 0.2 |
| Pb | 0.2 | 0.4 |

TABLE 2

| | First cycle of cleaning and sterilizing process | | Second cycle of cleaning and sterilizing process | | Build-up period (hr) |
|---|---|---|---|---|---|
| | Alkali cleaning | Sterilizing | Alkali cleaning | Sterilizing | |
| Example 1 | ○ | ○ | ○ | ○ | 20 |
| Comparative Example 1 | — | ○ | — | — | 1000 |
| Comparative Example 2 | ○ | ○ | — | — | 200 or more |
| Comparative Example 3 | ○ | — | ○ | ○ | 60 |
| Comparative Example 4 | ○ | ○ | — | ○ | 180 |
| Comparative Example 5 | — | ○ | ○ | ○ | 180 |

(○ the step was performed, — the step was not performed)

As shown in Table 1, in Example 1 in which the cleaning and sterilizing process including the cleaning with ammonia water and the sterilization with hydrogen peroxide water was made twice, the amount of metal impurities can be reduced to less than 0.5 ng/L when the build-up period is 36 hours, but in Comparative Example 2 in which the cleaning and sterilizing process including the cleaning with ammonia water and the sterilization with hydrogen peroxide water was made only once, a level of less than 0.5 ng/L cannot be achieved at after 36 hours. Furthermore, in Comparative Example 2, it took 240 hours to reduce the level to below 0.5 ng/L.

It is confirmed from Tables 1 and 2 that according to the present invention, the build-up period can be significantly shortened only by repeatedly treating the cleaning and sterilizing process including the cleaning with alkaline solution and the sterilization with sterile water twice or more.

Experimental Examples 1 to 6

The cleaning and sterilizing process was performed as in Example 1 except that flushing after the alkali cleaning treated under the same conditions (except that the flow rate of the ammonia water was about 1.0 m/sec) as those in the alkali cleaning in the first cycle of the cleaning and sterilizing process was made at various flushing water flow rates as shown in the following Table 3. The period of time of flushing necessary to reduce the pH of the flushing water in the channel 3b to 8 was investigated, and the period of time of the flushing in each experimental example was determined as a relative value by assuming the period of time of flushing when the flow rate of the flushing water was 2.0 m/sec as 1.0. The results are shown in Table 3 and FIG. 3.

Figure 3:
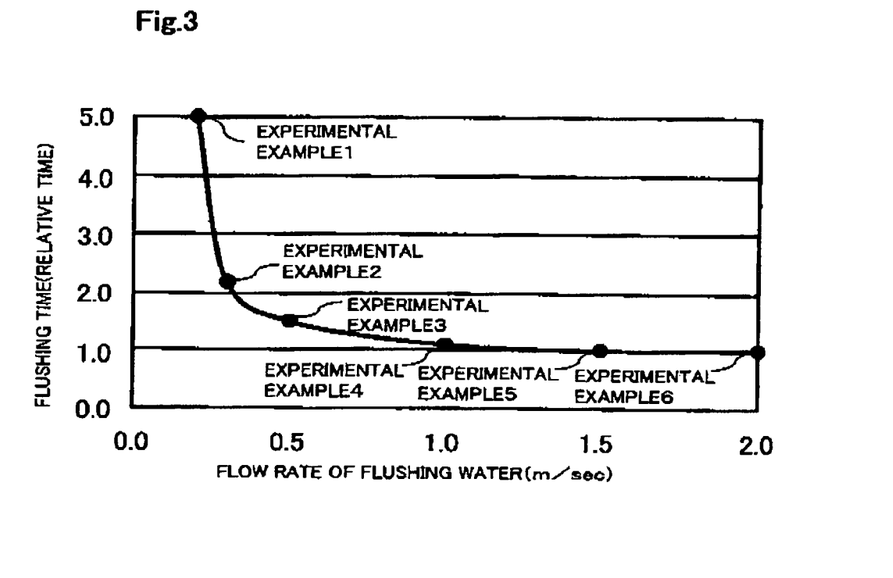
FIG. 3 is a graph showing a relationship between the flow rate during flushing and the period of time of the flushing in experimental examples 1 to 6.

These results reveal that efficient cleaning is possible by setting the flow rate in the flushing to 0.3 m/sec or more, in particular, 0.5 m/sec or more. Furthermore, it is confirmed that the cleaning efficiency is hardly increased at a flow rate higher than 1.5 m/sec.

TABLE 3

| | Flow rate (m/sec) | Flushing time (relative time) |
|---|---|---|
| Experimental example 1 | 0.2 | 5.0 |
| Experimental example 2 | 0.3 | 2.2 |
| Experimental example 3 | 0.5 | 1.5 |
| Experimental example 4 | 1.0 | 1.1 |
| Experimental example 5 | 1.5 | 1.0 |
| Experimental example 6 | 2.0 | 1.0 |

Experimental Examples 7 to 12

Differences in the number of particles in alkaline solution were investigated by treating the cleaning and sterilizing process under the same conditions as those in Example 1 except that the period of time of the alkali cleaning step in the first cycle of the cleaning and sterilizing process was variously changed. The number of particles having a diameter of 0.5 μm or more in the alkaline solution in each experimental example was measured by an on-line monitor, and relative values were determined by assuming the number of particles when the alkali cleaning step was treated for 2 hours as 1. The results are shown in Table 4 and FIG. 4.

TABLE 4

| | Cleaning time [hr] | Number of particles with a diameter of 0.5 μm or more [relative value] |
|---|---|---|
| Experimental example 7 | 0.25 | 0.15 |
| Experimental example 8 | 0.5 | 0.4 |
| Experimental example 9 | 1 | 0.8 |
| Experimental example 10 | 1.5 | 0.9 |
| Experimental example 11 | 2 | 1 |
| Experimental example 12 | 3 | 1.05 |

Figure 4:
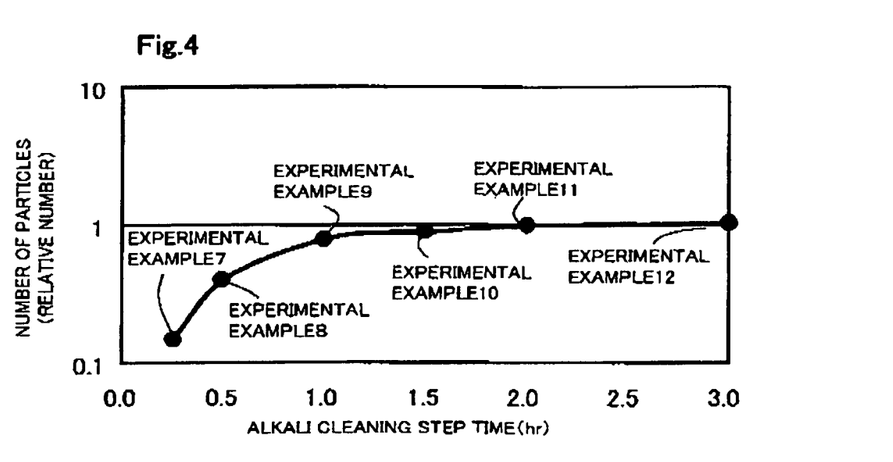
FIG. 4 is a graph showing a relationship between the period of time of the alkali cleaning step and the number (relative number) of particles in alkaline solution in experimental examples 7 to 12.

As shown in Table 4 and FIG. 4, it is confirmed that alkali cleaning is effectively performed when the period of time of the alkali cleaning step is 0.5 hours or more. However, it is also confirmed that the cleaning performance is not very increased when the period of time of the alkali cleaning step is excessively elongated.

Experimental Examples 13 to 18

Differences in the metal concentration in sterile water were investigated by treating the cleaning and sterilizing process under the same conditions as those in Example 1 except that the period of time of the sterilizing step in the first cycle of the cleaning and sterilizing process was variously changed. The metal concentration in the sterile water in each experimental example was measured by ICP-MS, and relative values were determined by assuming the metal concentration in the sterile water when the sterilizing step was treated for 2 hours as 1. The results are shown in Table 5 and FIG. 5.

TABLE 5

|  | Sterilizing time (hr) | Metal concentration (relative value) |
|---|---|---|
| Experimental example 13 | 0.25 | 0.2 |
| Experimental example 14 | 0.5 | 0.6 |
| Experimental example 15 | 1 | 0.9 |
| Experimental example 16 | 1.5 | 1 |
| Experimental example 17 | 2 | 1 |
| Experimental example 18 | 3 | 1 |

Figure 5:
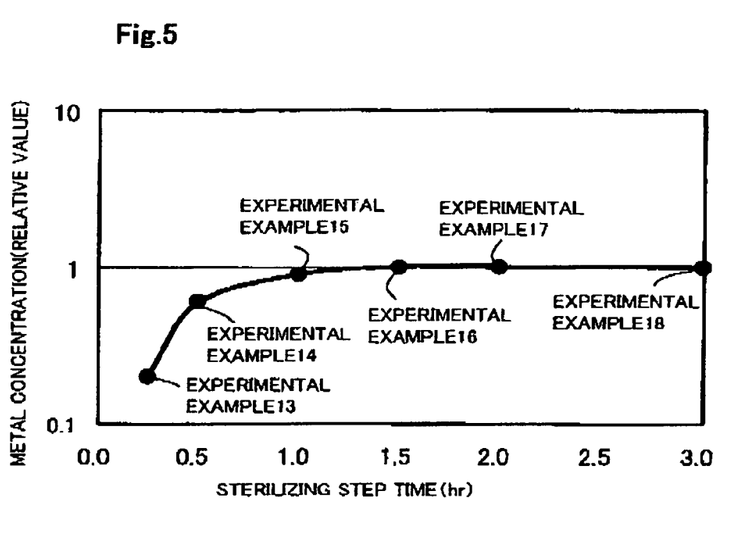
FIG. 5 is a graph showing a relationship between the period of time of the sterilizing step and the metal concentration (relative value) in sterile water in experimental examples 13 to 18.

As shown in Table 5 and FIG. 5, it is confirmed that sterilization is effectively performed when the period of time of the sterilizing step is 0.5 hours or more. However, it is also confirmed that the sterilization ability is not very increased when the period of time of the sterilizing step is excessively elongated.

The present invention has been described in detail with reference to specific embodiments, but it is obvious to those skilled in the art that various modifications are possible without departing from the spirit and the scope of the present invention.

The present application is based on Japanese Patent Application (Application No. 2007-91667) filed on Mar. 30, 2007, the entire contents of which are incorporated herein by reference.

The invention claimed is:

1. A method of cleaning and sterilizing an ultrapure water manufacturing apparatus, a point of use (POU) of ultrapure water, and an ultrapure water channel connecting the ultrapure water manufacturing apparatus and the point of use, the method comprising:
    an alkali cleaning step for supplying alkaline solution to at least part of an inside of the ultrapure water manufacturing apparatus, POU and ultrapure water channel and circulating the alkaline solution therein, thereby cleaning the at least part of the inside of the ultrapure water manufacturing apparatus, POU, and ultrapure water channel, followed by draining the alkaline solution from the at least part of the inside of the ultrapure water manufacturing apparatus, POU, and ultrapure water channel;
    a first flushing step for supplying water to the ultrapure water manufacturing apparatus, POU, and ultrapure water channel, thereby flushing the alkaline solution remained in the ultrapure water manufacturing apparatus, POU, and ultrapure water channel after the alkali cleaning step;
    a preparation step for preparing a sterilizing water by heating the water supplied in the first flushing step to a predetermined temperature or supplying hydrogen peroxide to the water supplied in the first flushing step; and
    a sterilizing step for circulating the sterilizing water in the ultrapure water manufacturing apparatus, POU, and ultrapure water channel, thereby sterilizing the ultrapure water manufacturing apparatus, POU and ultrapure water channel,
    wherein the cleaning and sterilizing steps are repeatedly performed twice or more.

2. The method according to claim 1, wherein the alkaline solution is an aqueous solution containing an ammonium salt and/or an hydroxide of an alkali metal and having a pH of 9 or more.

3. The method according to claim 1, wherein
    in the sterilizing step, the water is heated to the predetermined temperature of 60° C. or more, and
    the hydrogen peroxide has a hydrogen peroxide concentration of 0.01 to 10% by weight and a temperature of 10 to 50° C.

4. The method according to claim 1, wherein
    a period of time of the alkali cleaning step in a first cycle of the cleaning and sterilizing process is set to 0.5 hours or more, and
    the alkali cleaning step in a second or later cycle of the cleaning and sterilizing process is treated for a period of time longer than the alkali cleaning step in the first cycle of the cleaning and sterilizing process.

5. The method according to claim 1, wherein
    a period of time of the sterilizing step in a first cycle of the cleaning and sterilizing process is set to 0.5 hours or more, and
    the sterilizing step in a second or later cycle of the cleaning and sterilizing process is treated for a period of time longer than the sterilizing step in the first cycle of the cleaning and sterilizing process.

6. The method according to claim 1, wherein a flow rate of the alkaline solution used in the alkali cleaning step is set to 0.3 to 2.0 m/sec.

7. The method according to claim 1, wherein a flow rate of the water used in the first flushing step is set to 0.3 to 2.0 m/sec.

8. The method according to claim 1, wherein the first flushing step is carried on until a pH of the water is reduced to 8 or less and/or a resistivity of the water is increased to a predetermined value of 10 MΩ·cm or more.

9. The method according to claim 1, further comprising a second flushing step for supplying another water to the ultrapure water manufacturing apparatus, POU, and ultrapure water channel, thereby flushing the sterile water out from the ultrapure water manufacturing apparatus, POU and ultrapure water channel after the sterilizing step.

10. The method according to claim 1, wherein the water supplied in the first flushing step has a resistivity of 15 MΩ·cm or more, 1 μg/L or less of total organic carbon (TOC), and 1 ng/L or less of metals.

11. The method according to claim 1, wherein the water supplied in the first flushing step is raw water treated with a reverse osmosis membrane device and an ion exchanger.

12. The method according to claim 1, wherein the water supplied in the first flushing step has a resistivity of 10 MΩ·cm or more and 100 μg/L or less of total organic carbon (TOC).

13. The method according to claim 3, wherein the water supplied in the first flushing step has a resistivity of 15 MΩ·cm or more, 1 μg/L or less of total organic carbon (TOC), and 1 ng/L or less of metals.

14. The method according to claim 3, wherein the water supplied in the first flushing step is raw water treated with a reverse osmosis membrane device and an ion exchanger.

15. The method according to claim 3, wherein the water supplied in the first flushing step has a resistivity of 10 MΩ·cm or more and 100 μg/L or less of total organic carbon (TOC).

16. The method according to claim 9, wherein a flow rate of the another water used in the second flushing step is set to 0.3 to 2.0 m/sec.

* * * * *